(12) United States Patent
Canessa et al.

(10) Patent No.: US 7,120,644 B1
(45) Date of Patent: Oct. 10, 2006

(54) DIGITAL IMAGE STORAGE AND MANAGEMENT SYSTEM

(75) Inventors: John C. Canessa, Eagan, MN (US); Giancarlo Canessa, Eagan, MN (US); Gino G. Canessa, Eagan, MN (US); Shaoying Guan, St. Paul, MN (US)

(73) Assignee: Software Engineering Corporation, Bloomington, MN (US)

( * ) Notice: Subject to any disclaimer, the term of this patent is extended or adjusted under 35 U.S.C. 154(b) by 193 days.

(21) Appl. No.: 10/400,035

(22) Filed: Mar. 26, 2003

Related U.S. Application Data

(60) Provisional application No. 60/367,656, filed on Mar. 26, 2002.

(51) Int. Cl.
*G06F 17/30* (2006.01)

(52) U.S. Cl. .................. 707/102; 707/100; 707/101; 707/103 R; 707/104.1; 710/65; 700/234; 600/407; 382/128; 375/220

(58) Field of Classification Search ............. 707/7, 707/10, 100; 715/727, 853; 710/65; 700/234; 600/407; 382/128; 375/220
See application file for complete search history.

(56) References Cited

U.S. PATENT DOCUMENTS

| | | | | |
|---|---|---|---|---|
| 5,592,511 A | * | 1/1997 | Schoen et al. | 375/220 |
| 5,633,839 A | * | 5/1997 | Alexander et al. | 700/234 |
| 5,740,134 A | * | 4/1998 | Peterson | 700/234 |
| 5,920,317 A | * | 7/1999 | McDonald | 715/853 |
| 5,974,004 A | * | 10/1999 | Dockes et al. | 715/727 |
| 6,188,782 B1 | * | 2/2001 | Le Beux | 382/128 |
| 6,241,668 B1 | * | 6/2001 | Herzog | 600/407 |
| 6,529,757 B1 | * | 3/2003 | Patel et al. | 600/407 |
| 6,574,629 B1 | * | 6/2003 | Cooke et al. | 707/10 |
| 6,678,764 B1 | * | 1/2004 | Parvulescu et al. | 710/65 |
| 6,910,038 B1 | * | 6/2005 | James | 707/7 |
| 2002/0085476 A1 | * | 7/2002 | Samari-Kermani | 369/124.07 |
| 2004/0215637 A1 | * | 10/2004 | Kitamura et al. | 707/100 |

* cited by examiner

*Primary Examiner*—Frantz Coby
(74) *Attorney, Agent, or Firm*—Haugen Law Firm PLLP

(57) ABSTRACT

A digital image storage and management system for automatically generating distinct recorded media volumes by recording selected data thereon includes a combination of computer hardware and software components that are configured to operably receive and act upon user-defined commands delivered to the computer via a graphical user interface, which may be coupled to the computer through an external network. The hardware and software combination in the computer direct robotics to manipulate distinct recordable media volumes into and out from respective media recording drives. Data retrieved from local or distributed databases by the computer according to specific user-defined commands is compiled into discreet associated data sets and recorded onto one or more recordable media volumes. The computer also automatically creates a pre-defined association with the particular data set for cataloging purposes. The computer may also automatically direct a printing device to generate and install graphics onto a printable surface of the recorded media volume, which graphics may be uniquely associated with the data set recorded thereon.

9 Claims, 5 Drawing Sheets

DIGITAL IMAGE STORAGE AND MANAGEMENT SYSTEM

CROSS-REFERENCE TO RELATED APPLICATIONS

This application claims priority from provisional application Ser. No. 60/367,656, filed Mar. 26, 2002, the contents of which are herein incorporated in their entirety.

FIELD OF THE INVENTION

This invention relates generally to digital image storage and management, and more particularly to the field of volume generation using the Diagnostic Imaging and Communications in Medicine (DICOM) part ten (10) standard and labeling the resulting volumes using an electrically attached printer for the purpose of interchanging and archiving DICOM objects (i.e., images).

BACKGROUND OF THE INVENTION

Modern hospitals have implemented networks of various digital modalities such as a magnetic resonance (MR), computed tomography (CT), digital radiography, and ultrasound devices. These modalities, referred to as input imaging devices, produce vast numbers of diagnostic quality digital medical images. In order to more easily manage such images many hospitals are implementing a network of specialized equipment and components designed to support medical radiological imaging commonly referred to as a Picture Archiving and Communicating System (PACS). A PACS allows a radiologist to easily manage the large volume of digital medical images including archiving, retrieving, exchanging, displaying and manipulating images and associated reports. For example, when a patient is imaged by a medical modality, a series of digital images, referred to as a "series", is generated, captured and archived. A radiologist typically dictates a report that is later transcribed into some type of text document. A radiologist can easily and quickly retrieve the patient's series, or any previous series, and display the series on a display station for viewing. Furthermore, the retrieved study or series can be forwarded to another radiologist, perhaps located at a remote hospital. By easing the burden of managing digital medical images, PACS are expected to improve patient care and the efficiency of the radiology department. Furthermore, by integrating PACS with a Hospital Information Management System (HIS), patient information can be coupled with the study, thereby improving the efficiency of the hospital as a whole.

In order to facilitate archival and retrieval of medical images, a PACS typically incorporates a short-term storage device having a plurality of short-term storage media, such as RAID, NAS, OR SAN, which are typically rewritable media, and a long-term storage device having a plurality of long-term storage media, such as a tape or optical device archiving device capable of managing an automated or manual library of volumes. As new images and associated reports are generated from the various medical modalities, the system stores the images on the short-term storage device using a "best-fit" approach. In this manner, the system distributes the images across the plurality of short-term storage media in order to minimize wasted storage space. Thus, each image in a patient's series may be stored on unique media in order to most efficiently manage storage space. A central database maintains the location of each image. If a radiologist does not request a patient's series for a period of time, the system automatically moves the corresponding images to the long-term (near-line) storage device and updates the database. The PACS distributes the images of the series across the long-term storage media to minimize wasted storage space. When, for example, a radiologist or a radiology technician (i.e., a user) requests a particular patient's series, the system accesses the database to determine the current location of the patient's images and reports. If the desired images reside on long-term storage media within the long-term storage device, the PACS automatically retrieves the images and moves them to the short-term storage device.

Although the best-fit archival scheme typically used by a PACS provides the benefits discussed above, it also has many shortcomings. For example, because the best-fit method distributes images across a plurality of media, it does not readily allow patient records to be physically archived to a shelf or an off-site storage facility. When a radiologist requests images for a particular patient, the hospital staff may have to physically retrieve several media from archive. Even if all the necessary long-term storage media is currently loaded into the long-term storage device, the device must independently initialize each long-term storage medium for access. Thus, in certain scenarios, the best-fit method can greatly increase archive retrieval time, thus compromising the efficiency of the archival system and increasing the cost thereof. For the reasons stated above, and for other reasons stated below which will become apparent to those skilled in the art upon reading and understanding the present specification, there is a need for a digital image management system which reduces access time and which requires less intervention by system administrators.

SUMMARY OF THE INVENTION

As explained in detail below, the present invention is directed to an appliance incorporating both computer hardware and software that facilitates media interchange and archival with a unique method for generating volumes with printed labels for topic image and information association. As applied to medical environments, the system creates a "DICOM part ten volume" and manages medical images by modeling conventional hospital film archival and manipulation procedures.

In one embodiment, the invention provides a means for exporting a plurality of DICOM images and objects associated with a selected one of a plurality of patients. The user via a Graphical User Interface (GUI) selects one or more patients, studies, series, or images for which all associated images will be mastered, burned and labeled into one or more CD or DVD volumes. The recorded data is then embodied in particular media volumes for association with the topics stored thereon.

According to another aspect of the invention, an application entity selectively (i.e., modality scanner, viewing station, etc.) prints using a PRINT DICOM command one (1) or more images associated with a selected topic. The appliance of the present invention preferably masters, burns and labels a set of one (1) or more CD or DVD volumes, as required. Objects such as images are limited to a single media volume, as the DICOM 10 standard does not allow objects to span across multiple media volumes.

These and other features and advantages of the invention will become apparent from the following description of the preferred embodiments of the invention.

DETAILED DESCRIPTION OF THE PREFERRED EMBODIMENTS

In the following detailed description, references are made to the accompanying drawings that illustrate various specific preferred embodiments in which the invention may be practiced. Electrical, mechanical, programmatic and structural changes may be made to these embodiments without departing from the spirit and scope of the present invention. The following detailed description is, therefore, not to be taken in a limiting sense and the scope of the present invention is defined by the appended claims and their equivalents.

Figure 1:
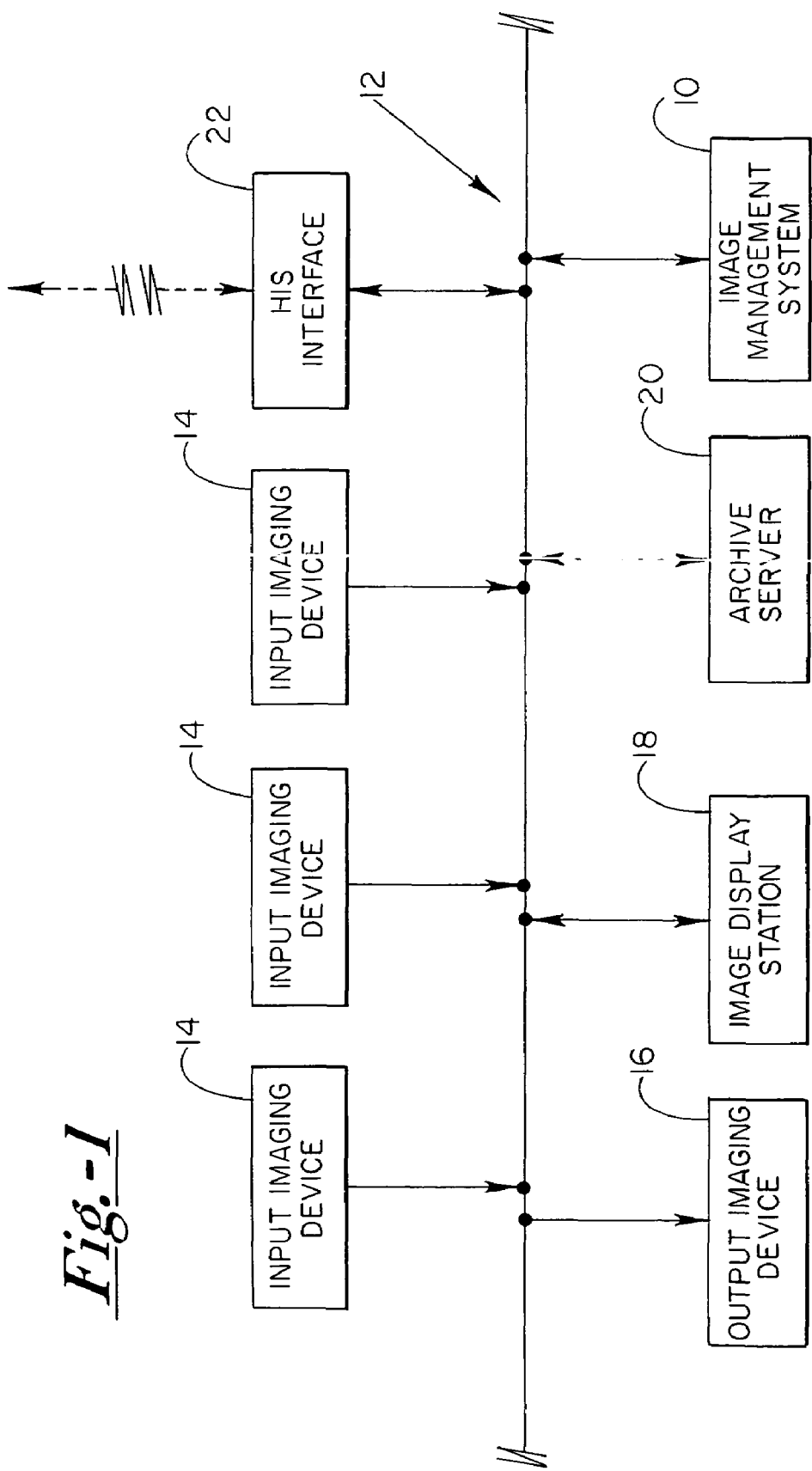
FIG. 1 is a schematic diagram of a digital image management system of the present invention having a plurality of input imaging devices, a plurality of image display stations, a plurality of output imaging devices and an archive server.

FIG. 1 illustrates a digital image management system 10 in accordance with a particular embodiment of the present invention that is operably coupled to one or more input imaging devices 14, one or more output imaging devices 16, one or more image display stations 18, and one or more archive servers 20 via an electronic network 12. Though the components listed and illustrated in FIG. 1 are preferably incorporated into the interconnected network 12, not all such components are required to be operably coupled to such network 12 for image management system 10 to operate as intended. Typically, however, image management system 10 of the present invention preferably communicates with network 12 to actively read and record selected data and data sets onto selected archival media, such as recordable optical devices, e.g. CDs or DVDs. Other recordable media may be utilized in combination with image management system 10 of the present invention in place of optical recordable media, as required.

In preferred embodiments of the present invention, network 12 is also operably coupled to a Hospital Information Management System (HIS) interface 22 to which an HIS is operably coupled for inputting and retrieving medical patient data to and from network 12. In such a manner, medical staff may remotely access network 12 and, correspondingly, image management system 10 for input and retrieval of patient text and image information. Such information may then be compiled by the HIS to provide medical staff with a compiled report on selected patients.

Each input imaging device 14, as illustrated in FIG. 1, may be an image-generating device capable of producing an electronic digital image. For example, in a medical imaging environment, input imaging devices 14 may be a variety of medical imaging modalities such as computed tomography (CT), digital radiography (DR), magnetic resonance (MR), and/or ultrasound (US) devices, manufactured by a number of different manufacturers, such as General Electric, Phillips, Siemens, or Toshiba. The digital images produced by input imaging devices 14 are communicated via network 12 to output imaging devices 16, display stations 18 or an archive server 20. In addition to communicating the generated images, the input imaging device 14 communicates topic-specific information. For example, in the medical environment input-imaging devices 14 may communicate a patient's name, a physician's name and a modality type. In one preferred embodiment, images are communicated over network 12 using a data communications protocol developed by the American College of Radiology (ACR) and the National Electrical Manufacturers Association (NEMA) known as the Digital Imaging and Communications in Medicine (DICOM) protocol. The DICOM protocol is typically implemented using a TCP/IP connection between the communicating devices in network 12.

The archive server 20 preferably stores each digital image received from network 12 according to the patient-specific information associated with the image. Such information and images are typically directed to archive server 20 either at predetermined short-term storage duration intervals, or upon manual commands of medical personnel that are transmitted to network 12 via the HIS and HIS interface 22. The archive server 20 initially stores the received image and other information on a "short-term" storage device (e.g. NAS, RAID). The archive server 20 preferably manages a database (not shown) in order to maintain information about each image including the database location of each image. The database may be centralized or distributed in that the database may be physically located within archive server 20, or may be remotely located and coupled to archive server 20 through a computer network such as the Internet.

Upon request by a user, such as a radiologist or radiology technician, the archive server 20 retrieves stored images and information from a corresponding database and communicates the information and images to respective display stations 18 for viewing. In addition, archive server 20 may communicate the retrieved images and/or reports to an output imaging device 16 to produce a hardcopy output of the retrieved image. In a medical environment, output imaging devices 16 may be continuous tone laser imagers for forming an image on an imaging element. In one preferred embodiment, output imaging devices 16 include a processor station (not shown) for chemical processing and developing of the output image formed a photographic element. In another such embodiment, the photographic element is photothermographic and can be thermally processed and need not be chemically processed. Other imaging processes are also suitable for output imaging devices 16 including direct thermal imaging, ablation imaging, dye transfer, ink jet, dye sublimation and thermal mass transfer. In yet another embodiment, the output imaging devices 16 operably coupled to the system of the present invention are used to master and burn (record) the images and information on a CD/DVD.

Figure 2:
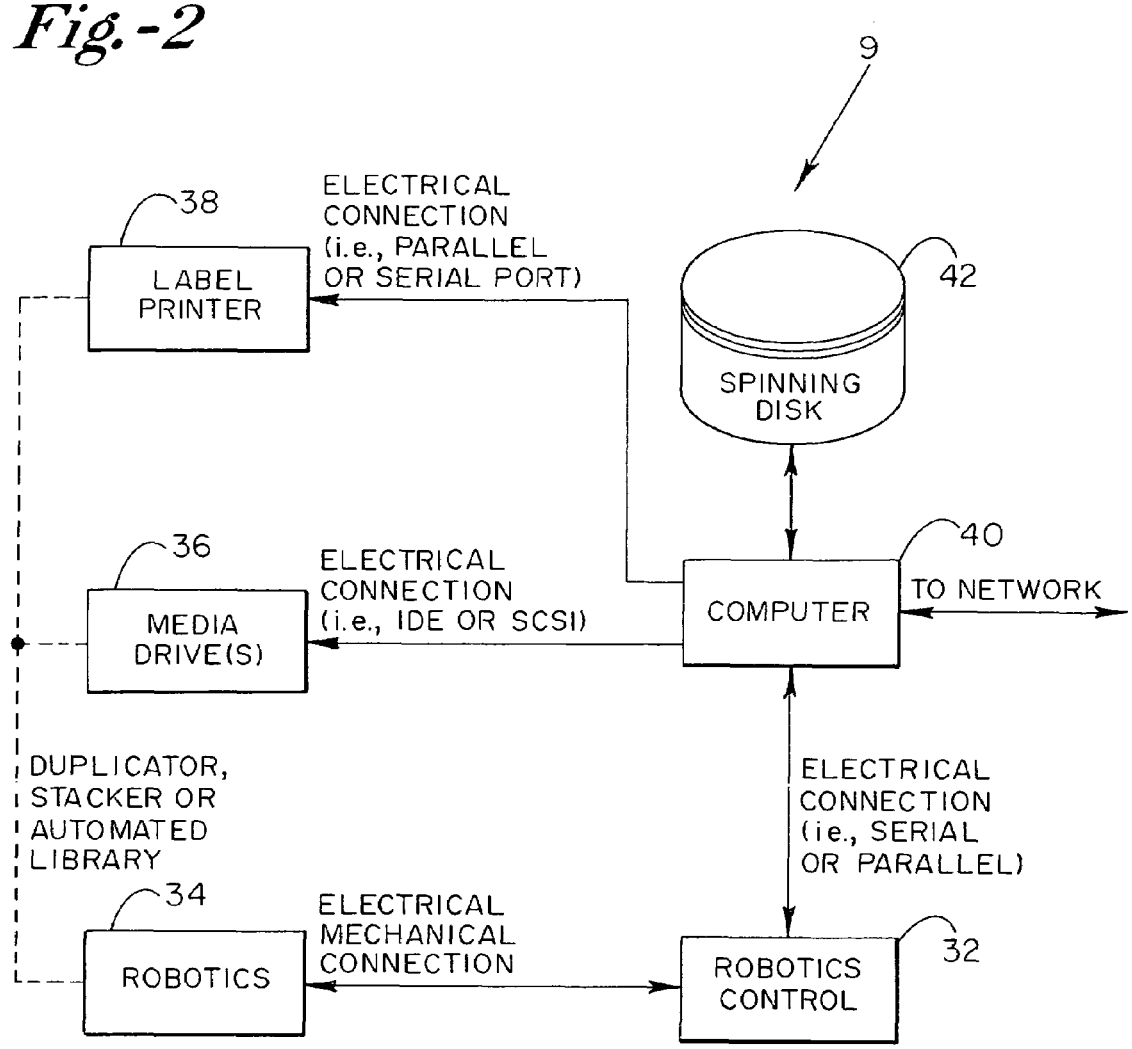
FIG. 2 is a block diagram of the hardware aspects of the present invention.

FIG. 2 illustrates the hardware modules, collectively hardware 9, for system 10 of the present invention in block diagram form. System 10, which may also be referred to as the interchange appliance, includes a robotics control module 32, the actual robotics 34, one (1) or more recordable media drives 36, and a label printer 38, all under operating control of a computer module 40 with spinning magnetic disk 42. Software executing on computer module 40 receives images and information and request commands from network 12. Based on such requests, the interchange appliance, using robotics control 32, orders robotics 34 to pick up a fresh recordable media volume from an input bin (not shown) and place such media volume in one of the recordable media drives 36. In particular, system 10 of the present invention is adapted to receive record or retrieve commands from network 12. However, a unique aspect of the present invention lies in the automated capability of system 10 to create physical recorded media containing distinct topics and associated information, including digital images corresponding to such topics. Such recorded media is then automatically labeled and electronically cataloged in a storage database of system 10, such that the recorded media volume may be physically archived as a primary or backup copy of the electronic data stored thereon. In applications wherein the recordable media volume represents a primary data storage location, the corresponding electronic data may be deleted to open up valuable electronic storage space for future use. Accordingly, system 10 of the present invention enables a network-driven and automated system for creating archival copies of electronic data, including digital images, on physical recorded media volumes. Moreover, the recorded data is automatically cataloged through at least one methodology, and preferably through multiple redundant methodologies. In particular, the recorded media volume is automatically physically labeled with information pertinent to cataloging and subsequent retrieval of the information stored thereon. Preferably, the recorded data is also electronically deposited into a database, and cataloged in such a manner so as to correlate with the archived recorded media volume.

After the recordable media volume is recorded upon, the robotics mechanism 34 moves the volume from recordable media drive 36 and places it into label printer 38. Label printer 38 images on a printable surface of the media volume text used to label the contents of the volume and, for example, one (1) or more images used for a background or different logos. The contents and positioning of the text and images are controlled by the software executing on computer 40 in the interchange appliance.

In preferred embodiments of the present invention, the one or more recordable media drives 36 utilized in hardware 9 are CD and/or DVD recordable drives, which are capable of both reading and recording ("burning") such CD/DVD media. It is highly preferred to utilize such optical recordable media for permanency purposes, in that such optical media exhibits substantial resistance to physical degradation over time. In other embodiments of the invention, however, recordable media such as magnetic tapes or the like may also or instead be utilized in corresponding recording drives.

As is further illustrated and detailed in FIG. 2, computer 40 is electrically coupled to robotics control 32, media drive 36, label printer 38, and disk 42, respectively. As such, instructions created in the software of computer 40 is transmitted to the respective control and operations components via electrical signals through such electrical connections. Preferably, robotics 34 are operably coupled to robotics control 32 through electromechanical connections, whereby electrical signals are transmitted from robotics control 32 and transformed into mechanical motion, which mechanical motion carries out the commands embodied in such electrical signals. In such a manner, robotics 34 physically move as a direct result of the electrical signals initiated by computer 40 through robotics control 32.

Figure 3:
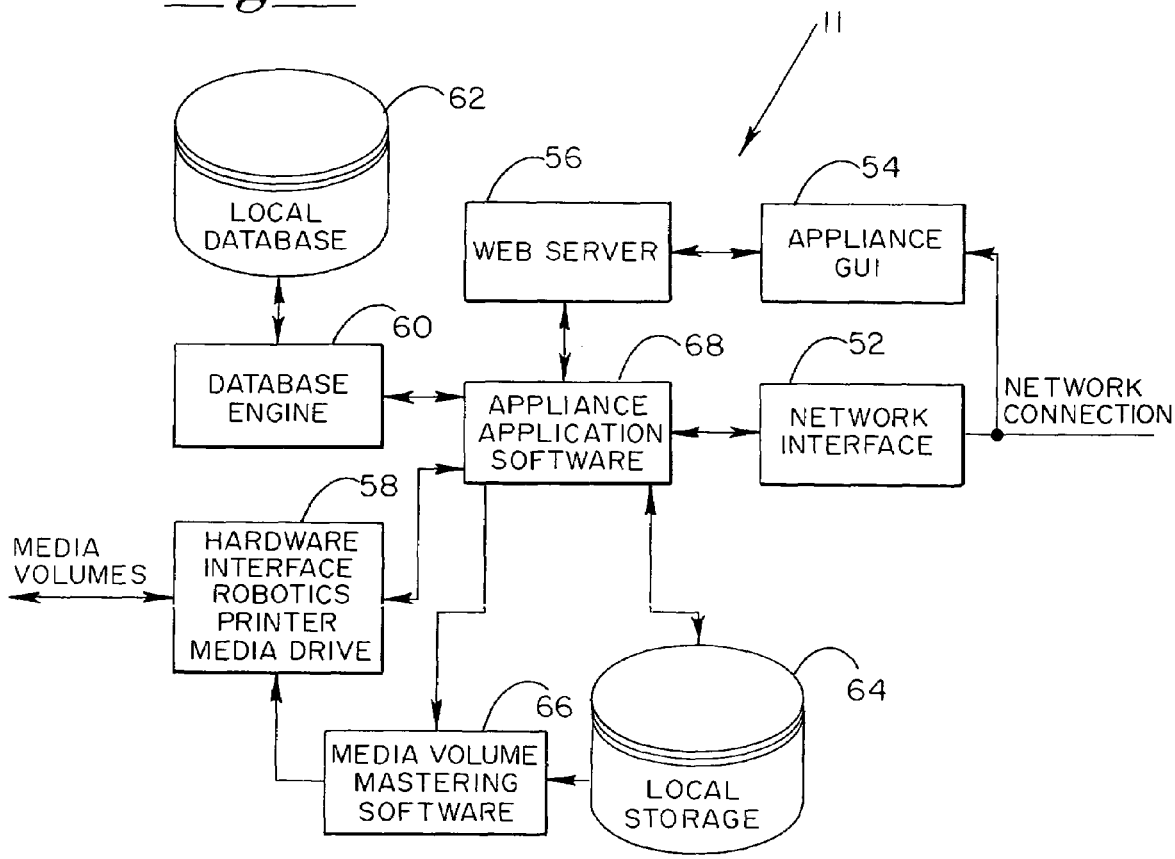
FIG. 3 is a block diagram showing the software aspects of the present invention.

FIG. 3 illustrates the software modules, collective software 11, for system 10 in block diagram form. Software 11 preferably includes a network interface module 52, a graphical user interface (GUI) 54, a web server 56 that renders the different pages for the GUI 54 on an appropriate software interface such as a browser for interface with one or more users simultaneously, hardware interface modules 58 used to control the operation of hardware 9, a database engine 60 for internal use, a local database 62 used to keep track of objects and recordable media volumes, local data storage modules 64 used to keep objects and data to be recorded onto or read from media, and recordable media mastering software 66 all under control of appliance application software 68.

With reference to FIG. 3, appliance application software 68 via network interface module 52 receives objects as a portion of a user retrieval/archive request. Such objects may be either images or structured data, sometimes in the form of reports. System 10 preferably appears on network GUIs as a selectable icon for MOVE and PRINT operations. The appliance implements storage and print service class providers. Typically, the objects are images grouped by topic, such as patient, study and series. Objects are sent to system 10 by other application entities on network 12. The application entities may use different commands to move or print images to system 10.

In one such embodiment, a user of system 10 via the HTML GUI executing over network 12 on a computer with an appropriate network interface such as a browser may query and retrieve images and other data from configured application entities over network 12. The user using standard network commands may move (push) a plurality of images and associated data to system 10. Using GUI 54 the user may select a set of images and/or data to be recorded onto one or more recordable media volumes. Multiple copies of the set may be specified via the same GUI 54.

A particular application contemplated by the present invention is the use of system 10 in combination with a DICOM network, such that system 10 is particularly adapted to receive commands according to the DICOM Part 10 standard, and to record data, including images, on recordable media volumes in compliance with the DICOM Part 10 standard. Therefore, system 10 may be advantageously utilized in combination with a pre-existing DICOM network incorporating an HIS and corresponding interface in medical environments. However, system 10 may also or instead be utilized in various applications that are capable of transmitting data through a network interface, and which data is desired to be archived in distinct and cataloged recordable media volumes.

Figure 4:
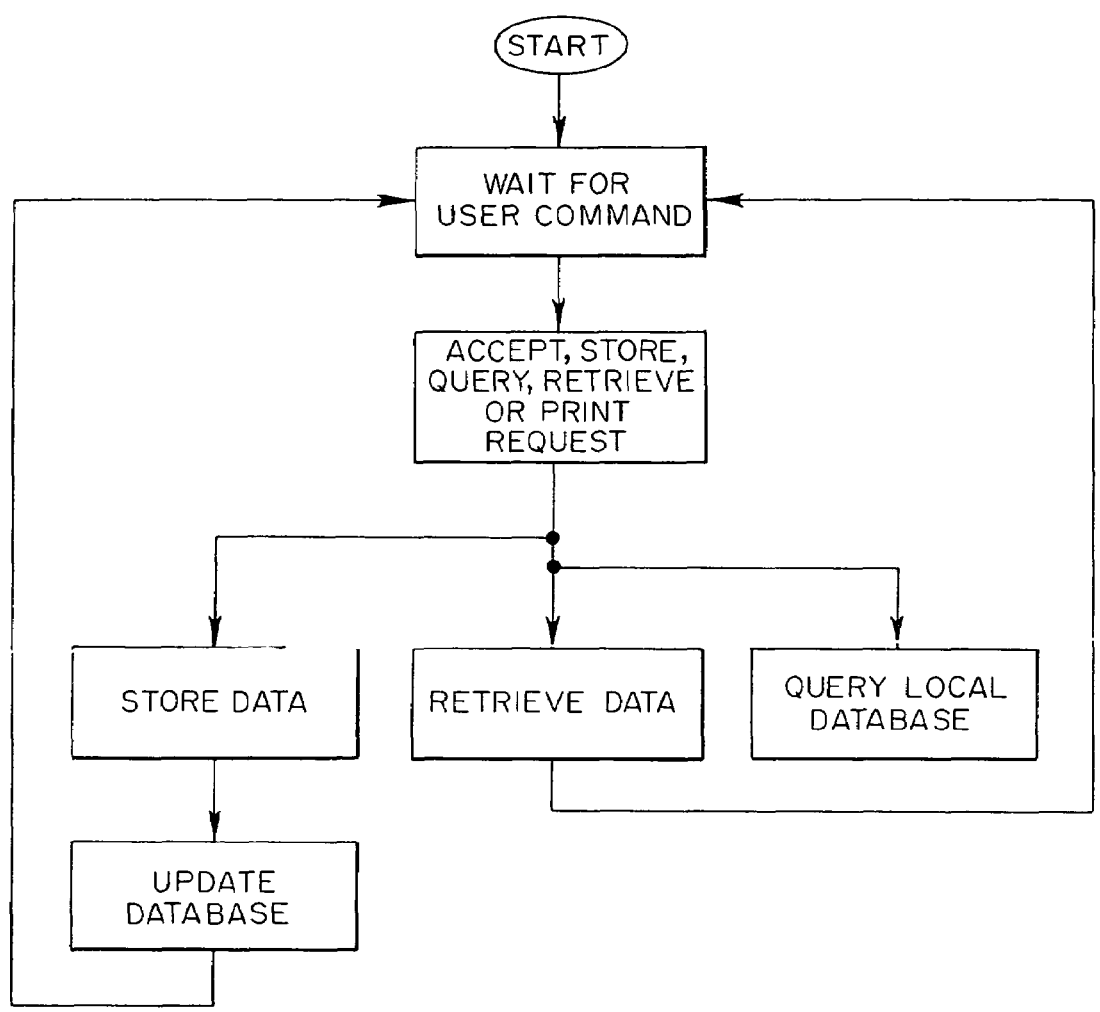
FIG. 4 is a flow chart illustrating a mode of operation of the Digital Image Storage and Management System in storing, printing, querying and retrieving images and structured reports in accordance with the present invention.

An example application is illustrated in FIG. 4 wherein system 10 waits for user instructions. After an instruction is accepted, software 11 selectively stores the associated objects and/or data, retrieves objects and/or data, or processes database queries using network-specific syntax and commands. After the subject objects and/or data are stored, database 62 is updated to reflect the new information contained therein.

Figure 5:
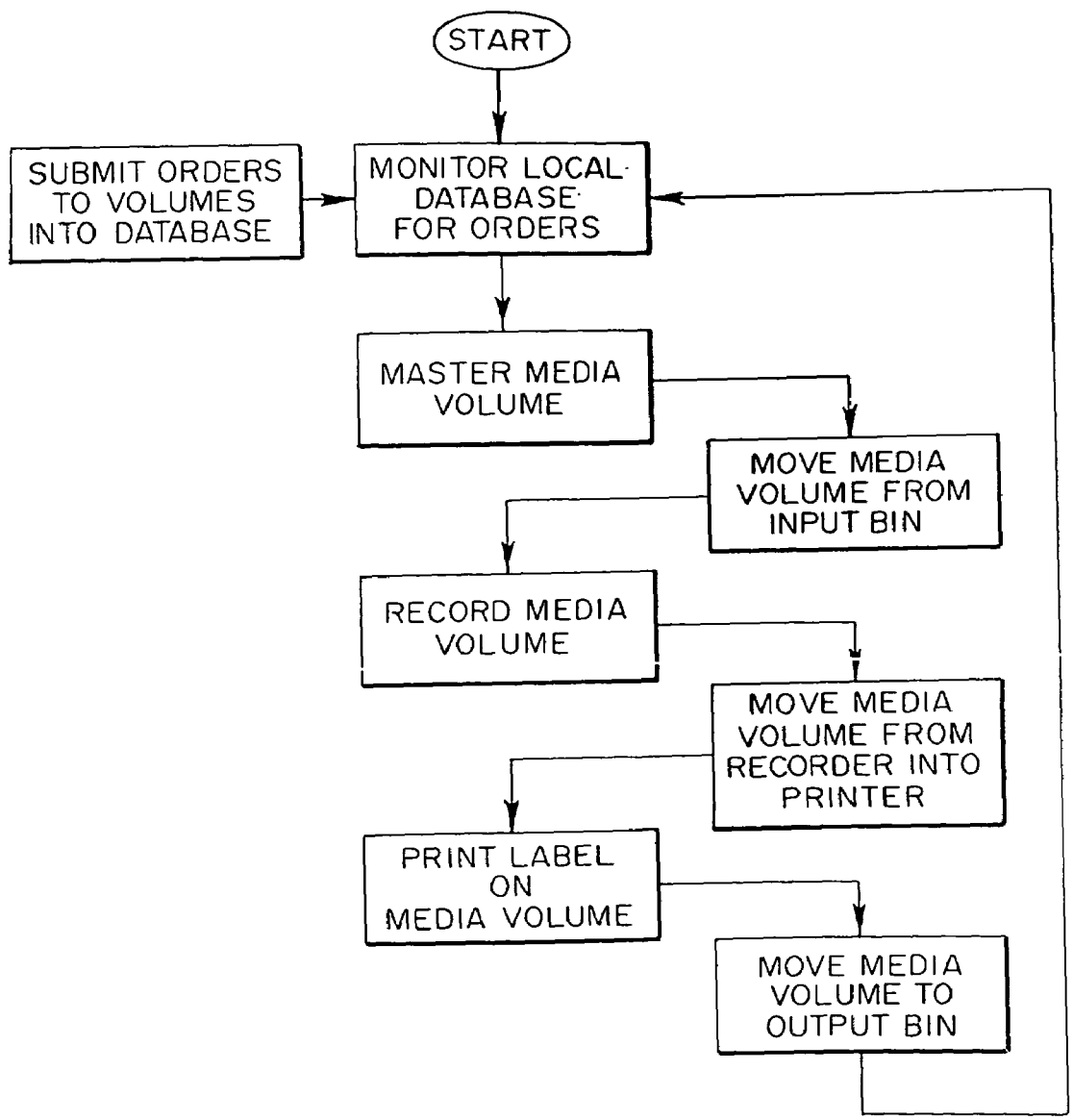
FIG. 5 is a flow chart illustrating a mode of operation of the Digital Image Storage and Management System in recording and printing media volumes with images and structured reports in accordance with the present invention.

FIG. 5 illustrates a method by which orders to generate recorded media volumes are processed by system 10 of the present invention. A GUI 54 accessed via a network interface from any computer on the respective network is used by customers to submit orders. Orders are inserted into local database 62. Orders are then processed sequentially using a priority scheme. An order is mastered by software 66 to fit into one (1) or more recordable media volumes. IN a particular embodiment, each volume is mastered following the DICOM Part 10 standard. Each such volume contains a DICOMDIR, a set of images, an ASCII file holding the comments for the volume and an image viewer. A fresh volume is moved from the input bin into one (1) of the recordable media drives 36. The volume is recorded therein.

Robotics 34 is then instructed by robotics control module 32 to move the volume from drive 36 to label printer 38. The printer prints a graphic directly on the surface of the media volume. After the print operation is completed, robotics 34 operably moves the volume from label printer 38 to an output bin/tray. Multiple orders may be processed simultaneously depending on the number of media drives 36 available in the unit.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. An automated system for generating and reading distinct DICOM standard compliant recorded media volumes, said system comprising:
   a first software means adapted to operably receive and interpret user-defined commands from a graphical user interface, said software means being operably coupled to a computer means, wherein said computer means operably executes such commands through at least said first software means;
   connection means operably connecting said computer means and said first software means to a database;
   a second software means operably coupled to said first software means and said computer means, and being adapted to arrange data retrieved from said database into defined data sets that are DICOM standard compliant;
   a robotics control means operably coupled to said first software means and said computer means for receiving electrical signals therefrom, said robotic control means being adapted to transform such electrical signals into control signals;
   robotics means operably coupled to said robotic control means and configured to physically carry out actions described in the control signals, said robotic means operably manipulating distinct said recordable media volumes by selectively inserting and removing said media volumes into and out from respective media read/write means, and depositing recorded said media volumes at desired locations, said media read/write means being operably coupled to said computer means, said first software means, and said second software means for operably receiving electrical signals therefrom, and being configured to interact with said media volumes, such interaction being selected from the group consisting of recording DICOM standard compliant data objects received from said second software means onto respective said media volumes, and retrieving DICOM standard compliant data objects from respective said media volumes,
   such that said system selectively retrieves data objects from said database, which data objects are pertinent to such user-defined commands, and automatically records DICOM standard compliant data onto one or more designated recordable media volumes, and retrieves DICOM standard compliant data objects from previously recorded media volumes.

2. An automated system as in claim 1, including labeling means operably coupled to said computer means and said first software means for operably creating graphics specifically associated with the data recorded on said respective media volume, and for operably affixing the graphics onto a surface of said respective media volume, such that said system automatically labels respective said volumes in such a manner so as to associate respective volumes with the data recorded thereon.

3. An automated system as in claim 1 wherein said first software means and said computer means are operably coupled to a computer network through a network interface.

4. An automated system as in claim 3 wherein one or more of said graphical user displays are remotely located with respect to said system, and are operably coupled thereto via the computer network and said network interface.

5. An automated system as in claim 3 wherein the computer network is a DICOM-compliant network.

6. An automated system as in claim 1, including electronic storage means operably coupled to said first software means and said computer means, said electronic storage means being configured to automatically save data operably retrieved from said database in an electronic format.

7. An automated system as in claim 6, including cataloging means for automatically associating a set of electronic data with the data recorded onto a respective distinct media volume, such that the data set is electronically defined as an individually selectable group.

8. An automated system as in claim 7 wherein said cataloging means automatically affixes one or more predefined codes to the electronic data set for subsequent retrieval of the individually selectable group via the predefined code associated therewith.

9. A method for automatically generating distinct recorded media volumes by recording selected DICOM standard compliant medical image data thereon, comprising:
   providing a computer means operably coupled to a computer network having one or more databases connected thereto, said computer means including software means being specifically configured and programmed to automatically control a robotics control module, a media recording means, and a labeling means, said robotics control module being adapted to receive signals from said computer means, and to transform such signals into motion directives delivered through electromechanical connections to selectively movable robotics;
   receiving a user-defined command from a graphical user interface operably coupled to the computer network;
   retrieving data pertinent to the user-defined command from said one or more network-connected databases;
   correlating the retrieved data into a distinct data set;
   formatting the data set into a DICOM Part 10 standard;
   directing said robotics control module to instruct said robotics to insert a distinct recordable media volume into said recording means;
   delivering the formatted data set to said recording means;
   instructing said recording means to record the formatted data set onto the media volume;
   instructing said robotics to remove the recorded media volume from said recording means, and to thereafter position the recorded media volume at said labeling means;
   instructing said labeling means to create graphics unique to the formatted data set, and to affix such graphics onto a surface of the recorded media volume; and
   instructing said robotics to move the recorded media volume to an output bin.

* * * * *